(12) United States Patent
Bae et al.

(10) Patent No.: US 9,585,596 B2
(45) Date of Patent: Mar. 7, 2017

(54) APPARATUS FOR CAPTURING MEDICAL IMAGE AND METHOD OF ADJUSTING TABLE THEREOF

(71) Applicant: Samsung Electronics Co., Ltd., Gyeonggi-do (KR)

(72) Inventors: Jin-hyun Bae, Gyeonggi-do (KR); Ji-hun Ahn, Incheon (KR)

(73) Assignee: Samsung Electronics Co., Ltd., Yeongtong-gu, Suwon-si, Gyeonggi-do (KR)

( * ) Notice: Subject to any disclaimer, the term of this patent is extended or adjusted under 35 U.S.C. 154(b) by 122 days.

(21) Appl. No.: 14/451,676

(22) Filed: Aug. 5, 2014

(65) Prior Publication Data

US 2015/0047125 A1    Feb. 19, 2015

(30) Foreign Application Priority Data

Aug. 13, 2013  (KR) .......................... 10-2013-0096129

(51) Int. Cl.
*A61B 5/055*    (2006.01)
*A61B 5/00*    (2006.01)
(Continued)

(52) U.S. Cl.
CPC ............ *A61B 5/0555* (2013.01); *A61B 5/706* (2013.01); *A61B 6/0407* (2013.01); *A61B 6/0492* (2013.01); *A61B 6/56* (2013.01); *G06K 7/10198* (2013.01); *A61B 6/03* (2013.01); *A61B 6/0457* (2013.01)

(58) Field of Classification Search
CPC ... A61B 5/0555; A61B 6/0407; A61B 6/0492; A61B 6/56; A61B 5/706; A61B 6/03; A61B 6/0457; G06K 7/10198
See application file for complete search history.

(56) References Cited

U.S. PATENT DOCUMENTS 6,416,219 B1 *   7/2002  Pflaum ................. A61B 6/0457
                                                                378/195
7,199,719 B2    4/2007  Steinberg
(Continued)

FOREIGN PATENT DOCUMENTS

JP           8-126638 A    5/1996
KR    10-2012-0096728 A    8/2012
KR    10-2013-0027235 A    3/2013

*Primary Examiner* — Robert G Santos
*Assistant Examiner* — Myles Throop
(74) *Attorney, Agent, or Firm* — Cha & Reiter, LLC

(57) ABSTRACT

A wireless device communicates with a medical image capturing apparatus to adjust a position of a table supporting an object to be imaged. An operator adjusts a position of the wireless device, the apparatus measures the wireless device's position, and adjusts the table based on the measured position. A method may include measuring distances between the wireless device and each of a plurality of respective detection units arranged along an axis. An axial distance may be measured between a reference point and the wireless device using measured distances and locations of the detection units relative to the reference point. The table is moved with respect to a gantry aperture of the apparatus based on the calculated axial distance. Controlled table movement may be movement into the gantry aperture and/or table height adjustment.

14 Claims, 10 Drawing Sheets

(51) Int. Cl.
*A61B 6/00* (2006.01)
*G06K 7/10* (2006.01)
A61B 6/03 (2006.01)
A61B 6/04 (2006.01)

(56) References Cited

U.S. PATENT DOCUMENTS

| | | | | |
|---|---|---|---|---|
| 7,835,785 | B2 * | 11/2010 | Scully | A61B 5/06 600/424 |
| 2002/0188194 | A1 | 12/2002 | Cosman | |
| 2006/0044147 | A1 * | 3/2006 | Knox | G01S 3/32 340/686.1 |
| 2007/0225588 | A1 * | 9/2007 | Steckner | A61B 5/0555 600/407 |
| 2008/0200926 | A1 * | 8/2008 | Verard | A61B 5/06 606/130 |
| 2009/0264735 | A1 | 10/2009 | Steckner | |
| 2010/0317968 | A1 | 12/2010 | Wright et al. | |
| 2011/0102149 | A1 * | 5/2011 | Lin | G06F 3/012 340/10.1 |
| 2012/0127976 | A1 * | 5/2012 | Lin | G01S 13/82 370/338 |
| 2012/0133487 | A1 * | 5/2012 | Murofushi | G06K 7/10079 340/8.1 |
| 2013/0060129 | A1 | 3/2013 | Lee et al. | |
| 2013/0165767 | A1 | 6/2013 | Darrow et al. | |
| 2013/0340165 | A1 * | 12/2013 | Dong | A61B 6/102 5/601 |
| 2013/0345718 | A1 * | 12/2013 | Crawford | A61B 17/025 606/130 |
| 2014/0088404 | A1 * | 3/2014 | Gross | A61B 5/0555 600/411 |

* cited by examiner

APPARATUS FOR CAPTURING MEDICAL IMAGE AND METHOD OF ADJUSTING TABLE THEREOF

CLAIM OF PRIORITY

This application claims the benefit of Korean Patent Application No. 10-2013-0096129, filed on Aug. 13, 2013, in the Korean Intellectual Property Office, the disclosure of which is incorporated herein in its entirety by reference.

BACKGROUND

1. Technical Field

The present disclosure relates generally to a medical imaging apparatus, and more particularly, to methods of adjusting a position of a table supporting an object (e.g., patient) to be imaged by the medical imaging apparatus.

2. Description of the Related Art

An apparatus for capturing a medical image is a device for obtaining an image of an inner structure of an object. A non-invasive type of examination apparatus shows detailed structures, inner tissues, fluids, etc. in a body. Examples of the apparatus include a magnetic resonance imaging (MRI) apparatus, a computed tomography (CT) apparatus, an ultrasonic apparatus, and an X-ray apparatus.

An MRI apparatus obtains a cross-sectional image of an object by representing with contrast an intensity of a magnetic resonance (MR) signal with respect to a radio frequency (RF) signal that is generated in a magnetic field having a predetermined intensity. For example, when an object is laid in a strong magnetic field and an RF signal that resonates only specific atomic nuclei (for example, hydrogen nuclei) is instantaneously emitted to the object and stopped, an MR signal is emitted from the specific atomic nuclei. The MR signal is received to derive an MR image. Unlike imaging apparatuses such as a CT apparatus in which obtaining of an image is dependent upon a direction of detection hardware, an MRI apparatus may obtain a two-dimensional (2D) image or a 3D volumetric image that may be obtained in any arbitrary orientation. Also, since an MRI apparatus may not expose radiation to an object and an examiner and may obtain an image having good contrast between soft tissues, the MRI apparatus may obtain a neurological image, an intravascular image, a musculoskeletal image, and an oncologic image in which clear representation of an abnormal tissue is important.

A CT apparatus obtains an X-ray image of an object taken around at least one axis of rotation. Since a CT apparatus may provide a cross-sectional image of an object, the CT apparatus has an advantage in that an inner structure of the object (for example, an organ such as a kidney or a lung) may be represented in a non-overlapping image, unlike a general X-ray apparatus.

Both an MRI apparatus and a CT apparatus include a gantry having a centralized aperture in which an object (e.g., a patient or object simulating a living body) is placed in order to capture a medical image. The object is supported on a table, the table is moved into the gantry, and the object on the table is imaged by using an RF coil, an X-ray tube, etc. included in the gantry.

Since there are various parts of an object to be imaged (referred to as imaging parts) such as a patient's head, leg, neck or abdomen, it is important to position an imaging part of the object at a reference point in a gantry, for example, at a central point in the gantry, in order to obtain a high quality medical image.

SUMMARY

The present disclosure provides an apparatus for capturing a medical image and a method of adjusting a location of a table by using the apparatus, which may enable a user to easily and accurately set a point of an object to be imaged (referred to as an imaging point).

According to an aspect, there is provided a method performed by an apparatus for capturing a medical image to adjust a location of a table that supports an object to be imaged. The method involves measuring respective distances between a plurality of detection units arranged along an axis and an operator-adjustable wireless device (with position adjustable by an operator). An axial distance on the axis is calculated between a reference point and the wireless device by using the measured distances and locations of the plurality of detection units relative to the reference point. The table is moved with respect to a gantry aperture of the apparatus based on the calculated axial distance.

The axis may be in a longitudinal direction of the table, and the table may be moved into the gantry aperture based on the calculated axial distance.

The axis may be in a direction normal to a major surface of the table, with the major surface being parallel to the ground, and the table may be moved by adjusting the height of the table based on the calculated axial distance.

In an embodiment, the axis is a first axis in a longitudinal direction of the table, the plurality of detection units are a plurality of first detection units, the calculated axial distance is a first axial distance, and moving the table comprises moving the table into the gantry aperture. In this embodiment, the method further includes measuring respective distances between the wireless device and a plurality of second detection units arranged along a second axis. A second axial distance is calculated on the second axis between the reference point and the wireless device using the distances between the plurality of second detection units and the wireless device and locations of the plurality of second detection units relative to the reference point. The moving of the table comprises adjusting a height of the table based on the calculated second axial distance.

The method may further include setting a point on the object which is separated by the calculated first axial distance from the reference point as an imaging point, wherein the moving includes moving the table such that the imaging point is located in the gantry.

The method may further include receiving an imaging point setting request from the device.

The calculating may include, after the calculating of the first axial distance is completed, transmitting a message informing that the setting of the imaging point has been completed to the device.

The moving of the table may include receiving a table movement request from the device.

The device may include a radio frequency identification (RFID) tag, and the plurality of detection units may include a plurality of RFID readers.

The measuring may include measuring a distance between each of the plurality of RFID readers and the RFID tag by using a time taken from when a first signal is emitted from each of the plurality of RFID readers to when a second signal emitted from the RFID tag is received by each of the plurality of RFID readers.

The apparatus may be a magnetic resonance imaging (MRI) apparatus or a computed tomography (CT) apparatus.

According to another aspect of the present disclosure, there is provided a method performed by a wireless device to adjust a location of a table that supports an object, the method including: activating a radio frequency identification (RFID) tag attached to the wireless device based on a first input of a user; receiving from an apparatus for capturing a medical image a message informing that setting of an imaging point has been completed based on a location of the wireless device identified by using an RFID reader of the apparatus; and transmitting a table movement request to the apparatus based on a second input of the user.

The method may further include, when the message is not received from the apparatus within a predetermined period of time after the RFID tag is activated, outputting a message requesting that the location of the wireless device be re-adjusted.

According to another aspect of the present disclosure, there is provided a non-transitory computer-readable recording medium having embodied thereon a program for executing the method.

According to another aspect of the present disclosure, there is provided an apparatus for capturing a medical image which adjusts a location of a table that supports an object, the apparatus including: a distance measurement unit that measures distances between a plurality of detection units that are arranged along a first axis and an device that is located at an arbitrary point by a user; an imaging point setting unit that calculates a distance on the axis between a reference point and the device by using the measured distances and locations of the plurality of detection units relative to the reference point; and a table control unit that moves the table with respect to a gantry of the apparatus based on the calculated first axial distance.

According to another aspect of the present disclosure, there is provided a wireless device for adjusting a location of a table that supports an object, the wireless device including: a user input receiving unit that receives a predetermined input of a user; a tag control unit that activates a radio frequency identification (RFID) tag attached to the wireless device based on a first input of the user; and a communication unit that receives from an apparatus for capturing a medical image a message informing that setting of an imaging point has been completed based on a location of the wireless device identified by using an RFID reader of the apparatus, and transmits a table movement request to the apparatus based on a second input of the user.

The wireless device may further include an output unit that, when the message is not received from the apparatus within a predetermined period of time after the RFID tag is activated, outputs a message requesting that the location of the wireless device be re-adjusted.

The wireless device may further include a light pointer that emits a narrow beam of light and indicates which point is indicated by the wireless device.

BRIEF DESCRIPTION OF THE DRAWINGS

The above and other features and advantages of the presently disclosed technology will become more apparent by describing in detail exemplary embodiments thereof with reference to the attached drawings in which like reference numerals indicate like components or features, wherein.

DETAILED DESCRIPTION

Figure 1:
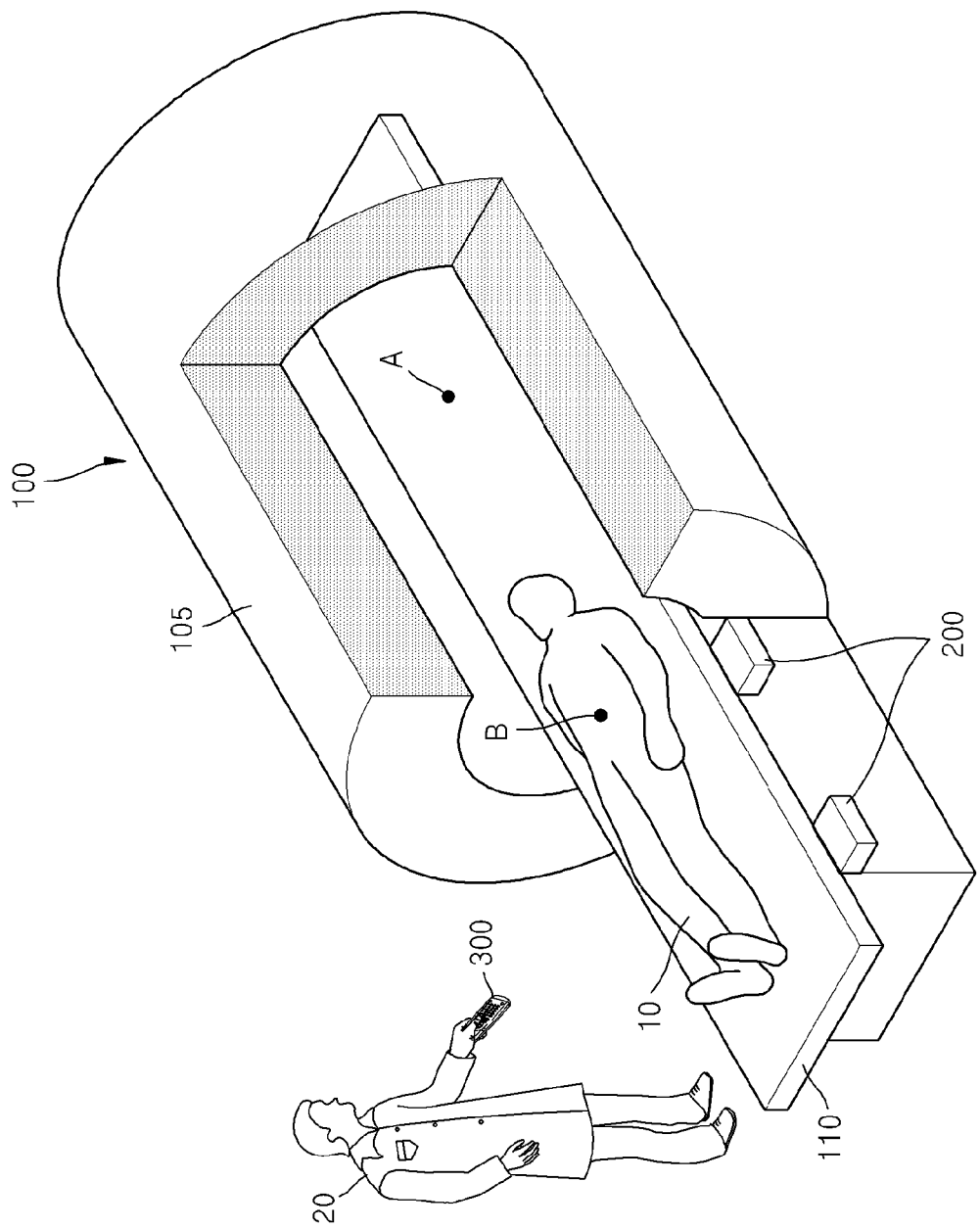
FIG. 1 is a perspective view illustrating an apparatus for capturing a medical image, according to an embodiment of the present disclosure.

Advantages and features of the presently disclosed technology and methods of achieving the advantages and features will be described more fully with reference to the accompanying drawings, in which exemplary embodiments of the disclosure are shown. The technology may, however, be embodied in many different forms and should not be construed as being limited to the embodiments set forth herein; rather these embodiments are provided so that this disclosure will be thorough and complete, and will fully convey the concept of the disclosure to one of ordinary skill in the art, and the scope of the present disclosure is defined only by the appended claims.

As used herein, the term "and/or" includes any and all combinations of one or more of the associated listed items. Expressions such as "at least one of," when preceding a list of elements, modify the entire list of elements and do not modify the individual elements of the list.

Terminology used herein will be briefly explained and then the present technology will be explained in detail.

Most of the terms used herein are general terms that have been widely used in the technical art to which the present disclosure pertains. However, some of the terms used herein may be created reflecting intentions of technicians in this art, precedents, or new technologies. Also, some of the terms used herein may be arbitrarily chosen by the present applicant. In this case, these terms are defined in detail below. Accordingly, the specific terms used herein should be understood based on the unique meanings thereof and the whole context of the present disclosure.

Throughout the present application, when a part "includes" an element, it is to be understood that the part additionally includes other elements rather than excluding other elements as long as there is no particular opposing recitation. The term "unit" in the embodiments of the present disclosure means a software-driven component or hardware components such as a field-programmable gate array (FPGA) or an application-specific integrated circuit (ASIC), and performs a specific function. However, the term "unit" is not limited to software or hardware. The "unit" may be formed so as to be in an addressable storage medium, or may be formed so as to operate one or more processors. Thus, for example, the term "unit" may refer to components such as software components, object-oriented software components, class components, and task components, and may include processes, functions, attributes, procedures, subroutines, segments of program code, drivers, firmware, micro codes, circuits, data, a database, data structures, tables, arrays, or variables. A function provided by the components and "units" may be associated with the smaller number of components and "units", or may be divided into additional components and "units".

"At least one of A and B" is used herein in order to select only A, select only B, or select both A and B. In addition, "at least one of A, B, and C" may be used in order to select only A, select only B, select only C, select only A and B, select only B and C, or select all of A, B, and C. It will be understood by one of ordinary skill in the art that the same applies even when more items are listed.

The term "image" used herein may refer to multi-dimensional data composed of discrete image elements (for example, pixels for two-dimensional (2D) images and voxels for three-dimensional (3D) images). For example, the image may include a medical image of an object obtained by using an X-ray system, a computed tomography (CT) system, a magnetic resonance imaging (MRI) system, an ultrasonic system, or any other medical imaging system.

The term "object" used herein may encompass a human, an animal, or a body part of a human or an animal. For example, the object may include an organ such as the liver, heart, womb, brain, breast, or stomach, or a blood vessel. Also, the "object" may be a phantom made of a material having a volume very similar to an effective atomic number and a density of a living creature and having properties similar to those of a human body.

The term "operator" used herein may refer to any operator of medical diagnostic equipment. An operator can be a technician, a medical expert such as a doctor, a nurse, a clinical pathologist, a medical image expert, or an engineer, etc.

The term "MRI image" used herein refers to an image of an object obtained by using nuclear magnetic resonance.

The term "pulse sequence" used herein refers to a series of signals that are repeatedly applied in an MRI apparatus. The pulse sequence may have radio frequency (RF)-pulse time parameters such as a repetition time (TR) and an echo time (TE).

The term "pulse sequence diagram" used herein refers to a diagram illustrating a sequence of events that occur in an MRI apparatus. For example, the pulse sequence diagram may be a diagram illustrating an RF pulse, a gradient magnetic field, or a magnetic resonance (MR) signal according to a time.

The term "CT image" used herein refers to a synthetic image of a plurality of X-ray images that are obtained by imaging an object around at least one axis of rotation.

FIG. 1 is a perspective view illustrating an apparatus 100 for capturing a medical image, according to an embodiment of the present disclosure. FIG. 1 exemplarily illustrates an MRI apparatus as the apparatus 100.

The apparatus 100 includes a table 110 that supports an object 10 (a person in this example), and a gantry 105 having an aperture in which the object 10 lying on the table 110 is placed.

In order to capture a medical image of the object 10, a body part or an imaging point B of the object 10 to be imaged is moved to a reference point A in the gantry 105 (i.e., in the gantry aperture), for example, at a central point in the gantry 105. Since there are many body parts of the object 10 which may be imaged, an operator 20 aids the apparatus 100 in recognizing a location of the desired body part or a predetermined imaging point B of the object 10 to be imaged.

A conventional method locates the imaging point B of the object 10 at a desired point to which a laser signal is emitted by a laser. The laser is located at a fixed point and sets the desired point as the imaging point B in the apparatus 100. However, this conventional method has a problem in that in order to locate the imaging point B at the desired point to which the laser signal is emitted, the operator has to manually adjust a location of the table 110.

Another conventional method divides the table 110 into a plurality of regions, allows the operator to select any one of the plurality of regions, and sets a location of the imaging point B in the apparatus 100. However, this conventional method has a problem in that the imaging point B of the object 10 is not accurately set.

The apparatus 100 of FIG. 1 may set the imaging point B of the object 10 by using a plurality of detection units 200 and a wireless device 300 that is manipulated by the operator 20. That is, the operator may conveniently and precisely set the imaging point B of the object 10 by using the wireless device 300 without manually adjusting a location of the table 110 on which the object 10 lies. As will be explained in detail below, in an implementation, the operator positions the device 300 at an axial point relative to the axis of the gantry 105 (the longitudinal direction of the generally oblong shaped table 110, referred to below as the Y axis). This axial point is at the same axial coordinate as the point B. The operator then inputs a command to set the imaging point. The detection units 200 measure the location of the device 300 at the axial point and thereby set the axial location of the imaging point B.

Although the plurality of detection units 200 are attached to the table 110 in FIG. 1, in other embodiments, the plurality of detection units 200 may be otherwise, connected, e.g., to a member that is connected to the top or bottom of the table 110.

Also, although an MRI apparatus is illustrated in FIG. 1, a method of setting the imaging point B by using the plurality of detection units 200 and the wireless device 300 may be similarly applied to a CT apparatus or other type of imaging apparatus.

Figure 2:
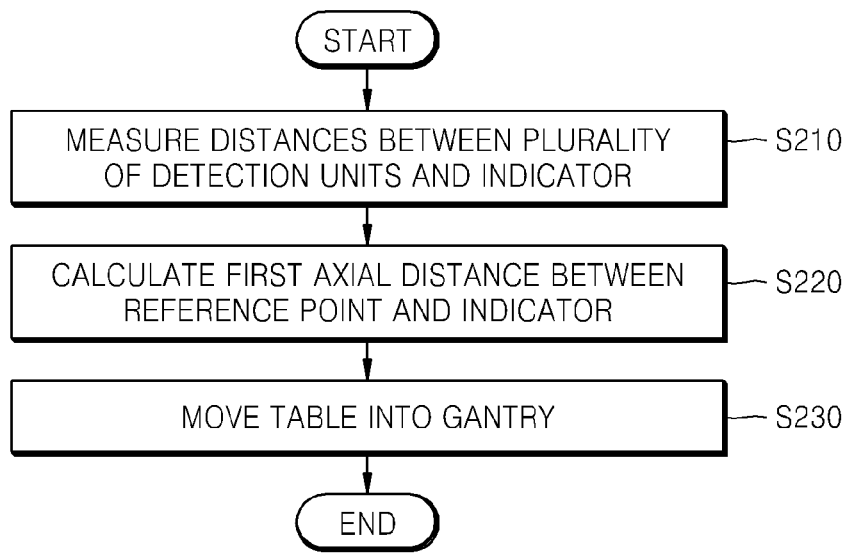
FIG. 2 is a flowchart illustrating a method of adjusting a location of a table, according to an embodiment of the present disclosure.

FIG. 2 is a flowchart illustrating a method of adjusting a location of the table 110, according to an embodiment of the present disclosure.

In operation S210, the apparatus 100 measures distances between the plurality of detection units 200 that are arranged along a first axis and the wireless device 300 that is positioned at an arbitrary point by the operator. For example, when a first detection unit 200-1 and a second detection unit 200-2 (refer to FIG. 3) are mounted parallel to a Y-axis and the operator holds the wireless device 300 at an arbitrary location, the apparatus 100 may measure a distance between the first detection unit and the wireless device 300 and a distance between the second detection unit and the wireless device 300.

The apparatus 100 may measure distances between the detection units 200 and the wireless device 300 by using various methods. For example, the apparatus 100 enables the detection unit 200 to transmit a distance measurement signal to the wireless device 300 and the wireless device 300 to receive the distance measurement signal, and then measures a time taken to transmit/receive the distance measurement signal. Next, the apparatus 100 may measure distances between the detection units 200 and the wireless device 300 by using the time taken to transmit/receive the distance measurement signal and a speed of the distance measurement signal. Examples of the distance measurement signal include an infrared signal, an ultrasound signal, and an RF signal.

Each of the detection units 200 may include a radio frequency identification (RFID) reader, and the wireless device 300 may include an RFID tag. The RFID reader may transmit an RF signal, may receive the RF signal reflected by the RFID tag as a response to the RF signal (or a response signal otherwise transmitted by the RF tag), and may identify the RFID tag. The apparatus 100 may measure a distance between the RFID reader and the RFID tag by using a time taken from when the RF signal is transmitted by the RFID reader to when the RF signal reflected by the RFID tag is received by the RFID reader, and a speed of the RF signal.

In operation S220, the apparatus 100 calculates a distance on the first axis (hereinafter, referred to as a first axial distance) between a reference point that is preset (e.g., by the operator) and the wireless device 300 by using the distances between the plurality of detection units 200 and the wireless device 300 and locations of the plurality of detection units 200 relative to the reference point. When the first axis is a Y-axis, the first axial distance indicates how far the wireless device 300 is separated along the Y-axis direction from the reference point. A method of calculating the first axial distance will be explained below with reference to FIG. 3.

In operation S230, the apparatus 100 moves the table 110 into the gantry 105 aperture based on the first axial distance.

As will be described below, since the operator may set the imaging point B of the object 10 just by positioning the wireless device 300 at a point that is separated in the Y-axis direction by the first axial distance from the reference point, the imaging point B may be more conveniently set than by using a conventional method.

Figure 3:
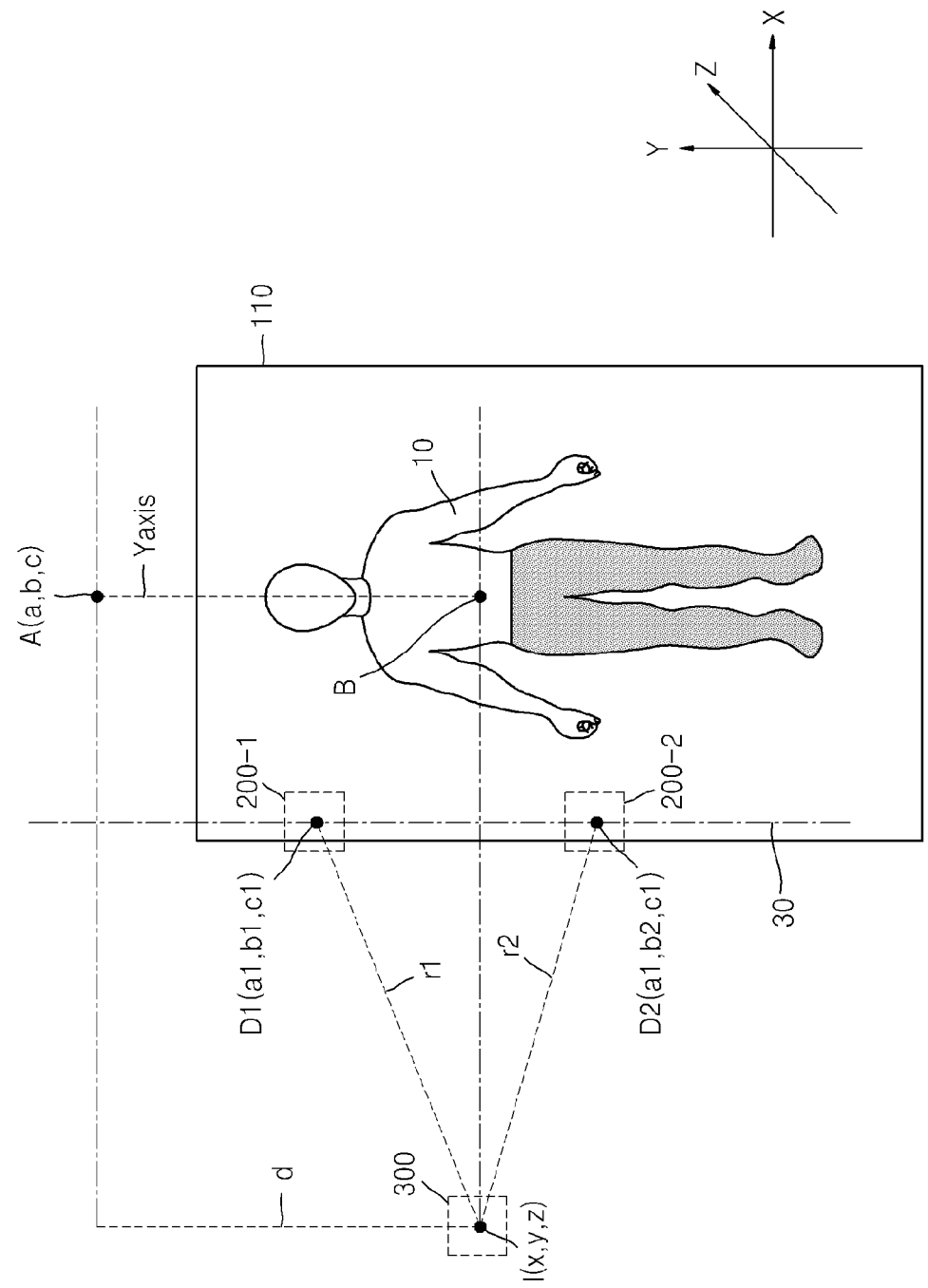
FIG. 3 is a view for explaining a method of setting an imaging point, according to an embodiment of the present disclosure.

FIG. 3 is a view for explaining a method of setting an imaging point, according to an embodiment of the present disclosure. A first detection unit 200-1 is located at a point D1 on a first axis 30 parallel to the Y axis, and the second detection unit 200-2 is located at a point D2 on the first axis 30. The Y axis is assumed to be in the lengthwise direction of the generally rectangular table 110, the X axis is assumed to be in the widthwise direction of table 110, and the Z axis is assumed in the height direction of the table with respect to the ground. Y coordinates of the points D1 and D2 are respectively b1 and b2. X and Z coordinates of each of the points D1 and D2 are a1 and c1, respectively.

A reference point is located at a point A. A location of the reference point can be pre-determined by the operator. The wireless device 300 is located at a point I(x, y, z).

As described above, distances between the wireless device 300 and each of the first and second detection units are measured. A distance between the points D1 and the point I is r1 and a distance between the point D2 and the point I is r2.

The apparatus 100 may calculate a first axial distance 'd' between the points A and I based on the distances r1 and r2 and locations of the points D1 and D2 relative to the point A. The locations of the points D1 and D2 relative to the point A are specified with coordinates (a1, b1, c1) of the point D1 and coordinates (a1, b2, c1) of the point D2 relative to point A.

The distance r1 between the points D1 and I may be defined by Equation 1, and the distance r2 between the points D2 and I may be defined by Equation 2.

$$r1^2 = (a1-x)^2 + (b1-y)^2 + (c1-z)^2 \quad (1).$$

$$r2^2 = (a1-x)^2 + (b2-y)^2 + (c1-z)^2 \quad (2).$$

Equation 3 is derived by subtracting Equation 1 from Equation 2.

$$r2^2 - r1^2 = (b2-y)^2 + (b1-y)^2 \quad (3).$$

In Equation 3, since r1, r2, b1, and b2 are values known from the distance measurements, a Y coordinate of the point I may be obtained from Equation 3. Finally, since a Y coordinate of the point A is b, the first axial distance 'd' between the points A and I may be calculated by subtracting y from b. In other words, the distance d is a length component in the Y-axis direction of the distance between the points I and A.

The apparatus 100 may set a point B on the object 10 which is separated by the first axial distance 'd' from the point A as an imaging point. Next, the apparatus 100 may move the table 110 into the gantry 105 so that the point B is located at the point A.

Since the table 110 may not move along an X-axis or a Z-axis in a general MRI apparatus, a location of the table 110 on the Y-axis is important. That is, the operator of the apparatus 100 may conveniently set an imaging point by positioning the wireless device 300 considering only a location of the imaging point on the Y-axis without considering its location on the X-axis and the Z-axis.

Figure 4:
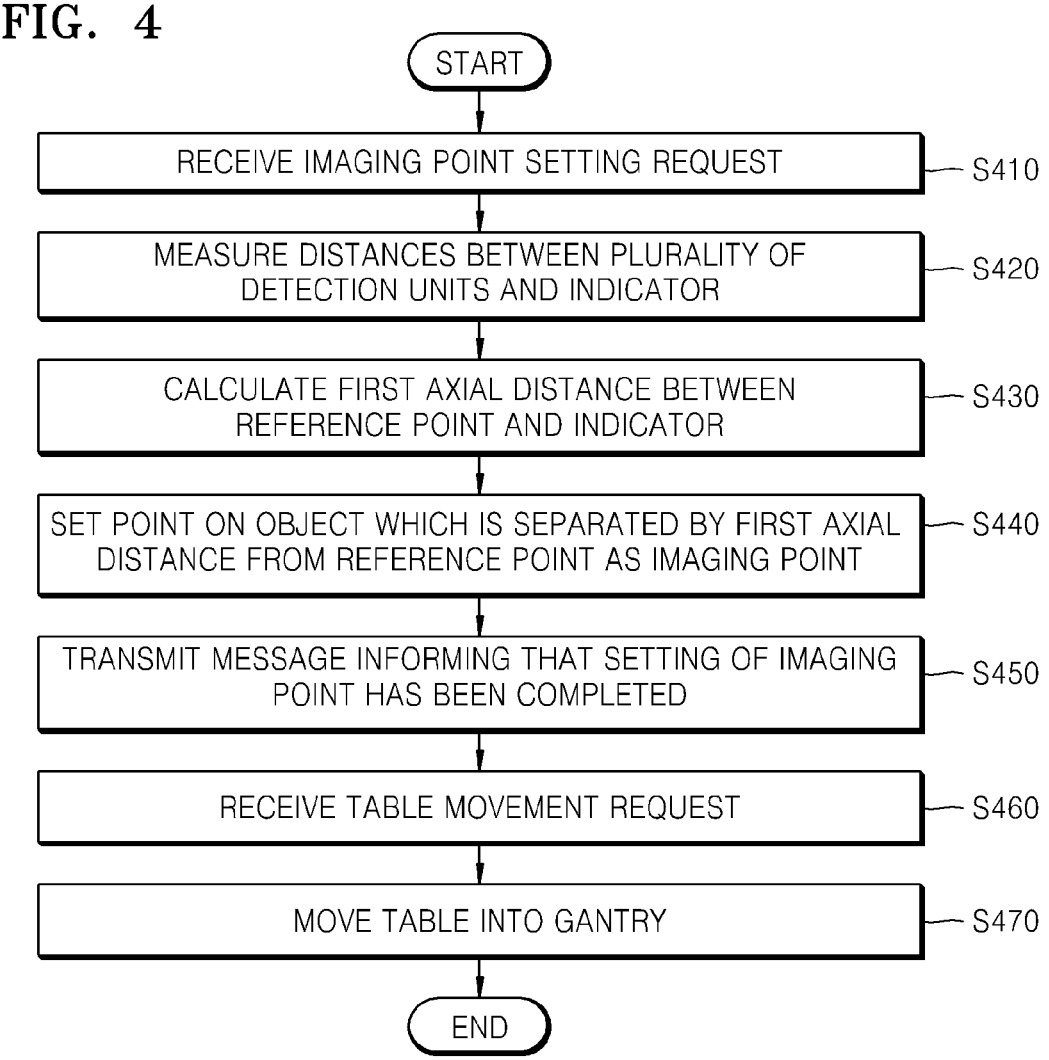
FIG. 4 is a flowchart illustrating a method of adjusting a location of the table, according to another embodiment of the present disclosure.

FIG. 4 is a flowchart illustrating a method of adjusting a location of the table 110, according to an embodiment. In operation S410, the apparatus 100 receives an imaging point setting request through the wireless device 300 from the operator. The operator may position the wireless device 300 at an arbitrary point in order to set an imaging point, and then may transmit the imaging point setting request to the apparatus 100 through a user input unit that is provided on the wireless device 300.

In operation S420, the apparatus 100 measures distances between the plurality of detection units 200 and the wireless device 300. In operation S430, the apparatus 100 calculates a first axial distance between a reference point and the wireless device 300. Methods performed by the apparatus 100 to measure distances between the plurality of detection units 200 and the wireless device 300 and to calculate a first axial distance between a reference point and the wireless device 300 have already been explained, and thus a detailed explanation thereof is omitted here.

In operation S440, the apparatus 100 sets a point on the object 10 which is separated by the first axial distance from the reference point as an imaging point.

In operation S450, the apparatus 100 transmits a message informing that the setting of the imaging point has been completed to the wireless device 300.

In operation S460, the apparatus 100 receives a table movement request from the operator through the wireless device 300. The operator may transmit the table movement request to the apparatus 100 through a user input unit that is provided on the wireless device 300.

In operation S470, the apparatus 100 moves the table 110 into the gantry 105 based on the first axial distance.

In FIG. 4, since the operator may control an imaging point to be set and the table 110 to be moved by using the wireless device 300, user convenience may be further improved.

Figure 5:
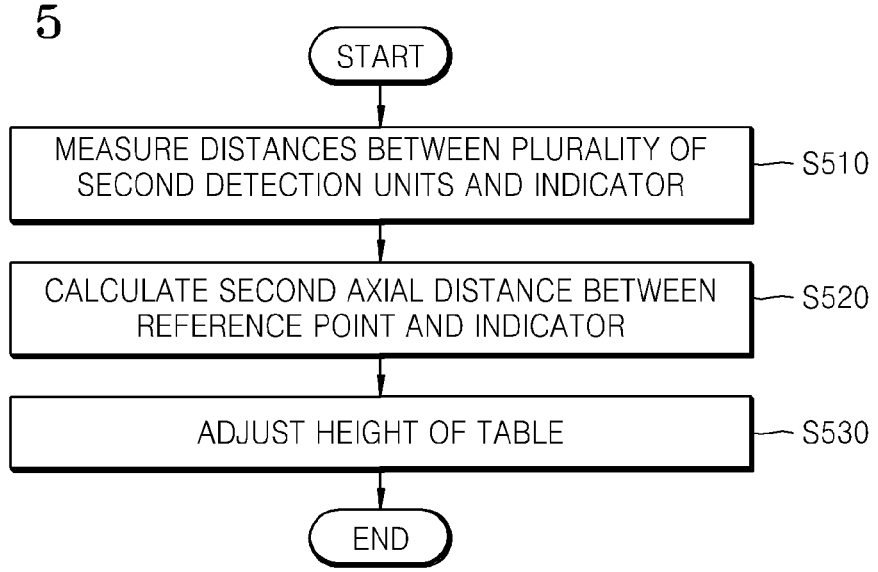
FIG. 5 is a flowchart illustrating a method of adjusting a location of the table, according to another embodiment of the present disclosure.

FIG. 5 is a flowchart illustrating a method of adjusting a location of the table 110, according to another embodiment of the present disclosure.

In operation S510, the apparatus 100 measures distances between a plurality of second detection units that are arranged along a second axis different from the first axis and the wireless device 300. The second axis and the first axis may be perpendicular to each other (the second axis may be the Z axis, i.e., in the height direction of the table 110). Any one of the plurality of second detection units may be the same as any one of the plurality of detection units described with reference to FIG. 2. That is, any one of the plurality of detection units that are arranged along the first axis may also be a second detection unit that is disposed along the second axis. (For example, the detection units may be mechanically movable from an arrangement arrayed along the Y axis to an arrangement arrayed along the Z axis.)

In operation S520, the apparatus 100 calculates a distance on the second axis (hereinafter, referred to as a second axial distance) between the reference point and the wireless device 300 by using the distances between the plurality of second detection units and the wireless device 300 and locations of the plurality of second detection units relative to the reference point. A method performed by the apparatus 100 to calculate the second axial distance will be explained below in detail with reference to FIG. 6.

In operation S530, the apparatus 100 adjusts a height of the table 110 based on the second axial distance. In a CT apparatus or an MRI apparatus in which a height of the table 110 is adjusted, when a height of an imaging point is the same as a height of the reference point in the gantry 105, image quality is ensured and it is important in adjusting the amount of X-ray radiation exposed to the object 10.

Figure 6:
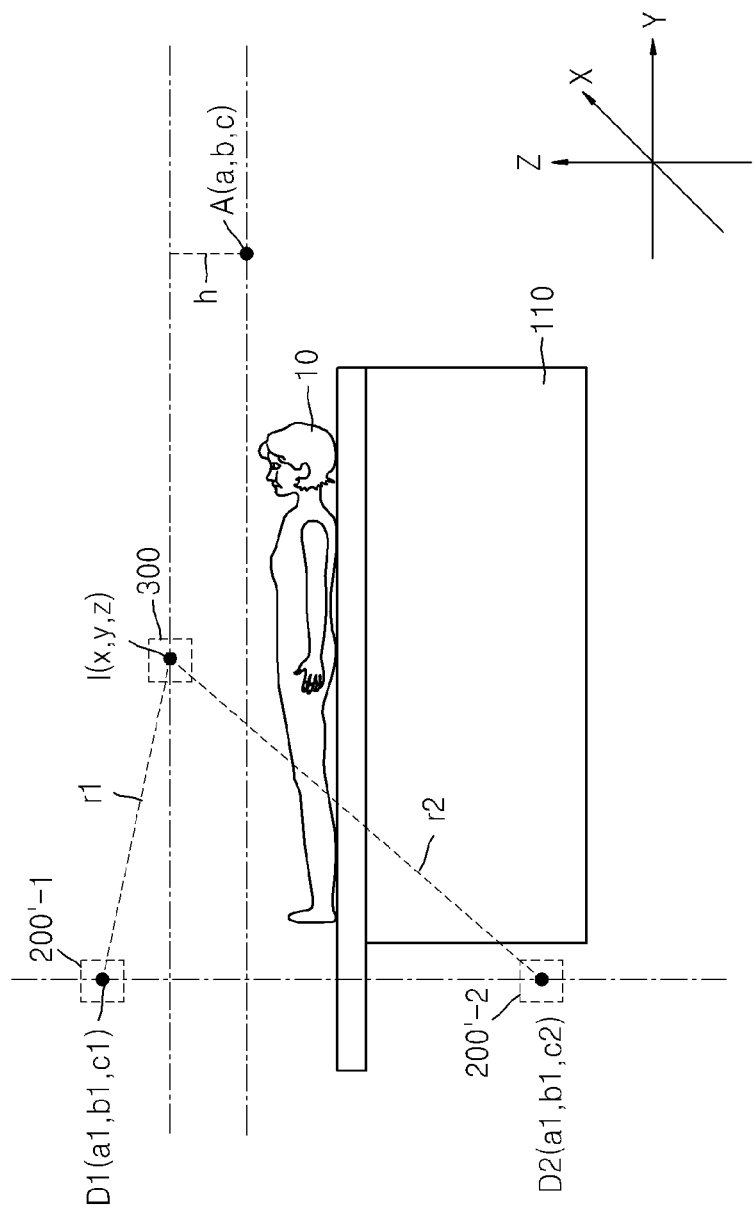
FIG. 6 is a view for explaining a method of setting an imaging point, according to another embodiment of the present disclosure.

FIG. 6 is a view for explaining a method of setting an imaging point, according to another embodiment of the present disclosure.

A first detection unit 200'-1 is located at a point D1 on a Z-axis; a second detection unit 200'-2 is located at a point D2 on the Z-axis. Z coordinates of the points D1 and D2 are respectively c1 and c2, X and Y coordinates (a1 and b1, respectively) of each of the points D1 and D2 are the same.

A reference point is located at a point A. A location of the reference point is pre-determined by the operator. The wireless device 300 is located at a point I.

As described above, a distance between detection unit 200'-1 and the wireless device 300 and a distance between detection unit 200'-2 and the wireless device 300 are measured. A distance between the points D1 and I is r1, and a distance between the points D2 and I is r2.

The apparatus 100 may calculate a second axial distance 'h' between the points A and I based on the distance r1 between the points D1 and I and the distance r2 between the points D2 and I, and locations of the points D1 and D2 relative to the point A. The locations of the points D1 and D2 relative to the point A are specified with coordinates (a1, b1, c1) of the point D1 and coordinates (a1, b1, c2) of the point D2.

A Z coordinate of the point I may be obtained by using Equations 1, 2, and 3. Since a Z coordinate of the point A is c, the second axial distance 'h' between the points A and I may be calculated by subtracting c from z.

The apparatus 100 may set a point that is separated by the second axial distance along the second axis from the point A as an imaging point. In the example, the apparatus 100 may lower the table 110 along the second axis by the second axial distance 'h' so that a height of the wireless device 300 (and a desired imaging point of the object 10) is the same as a height of the point A.

It is noted here that, as illustrated in FIG. 6, the second axis is in a direction normal to a major surface of the table, with the major surface being parallel to the ground, and the table may be moved by adjusting the height of the table based on the calculated axial distance.

Figure 7A:
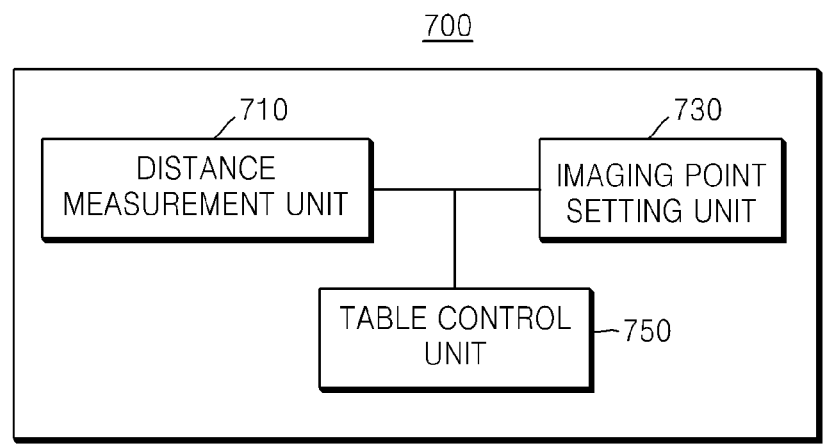
FIG. 7A is a block diagram illustrating elements of an apparatus for capturing a medical image, according to an embodiment of the present disclosure.

FIG. 7A is a block diagram illustrating elements of an apparatus 700 for capturing a medical image, according to an embodiment of the present disclosure. Apparatus 700 may be disposed within the gantry 105, and includes a distance measurement unit 710, an imaging point setting unit 730, and a table control unit 750. Each of the distance measurement unit 710 and the imaging point setting unit 730 may be embodied as a microprocessor.

The distance measurement unit 710 measures distances between the plurality of detection units 200 arranged along a first axis and the wireless device 300 positioned at an arbitrary location by the operator. The distance measurement unit 710 may measure a distance between each of the plurality of detection units 200 and the wireless device 300 by using a time taken from when a distance measurement signal is transmitted from each of the plurality of detection units 200 to when the distance measurement signal reflected by the wireless device 300 is received by each of the plurality of detection units 200. The distance measurement unit 710 may measure distances between a plurality of second detection units that are arranged along a second axis (e.g., perpendicular to the first axis) and the wireless device 300.

The imaging point setting unit 730 calculates a distance on the first axis (hereinafter, referred to as a first axial distance) between a reference point that is preset by the operator and the wireless device 300 by using the distances between the plurality of detection units 200 and the wireless device 300 and locations of the plurality of detection units 200 relative to the reference point. The imaging point setting unit 730 may set a point on the object 10 as an imaging point, which is spaced from the reference point by the first axial distance.

Also, the imaging point setting unit 730 may calculate a distance on the second axis (hereinafter, referred to as a second axial distance) between the reference point and the wireless device 300 by using the distances between the plurality of second detection units and the wireless device 300 and locations of the plurality of second detection units relative to the reference point.

The table control unit 750 moves the table 110 into the gantry 105 aperture of the apparatus 700 based on the calculated first axial distance. Also, the table control unit 750 may adjust a height of the table 110 based on the second axial distance.

Figure 7B:
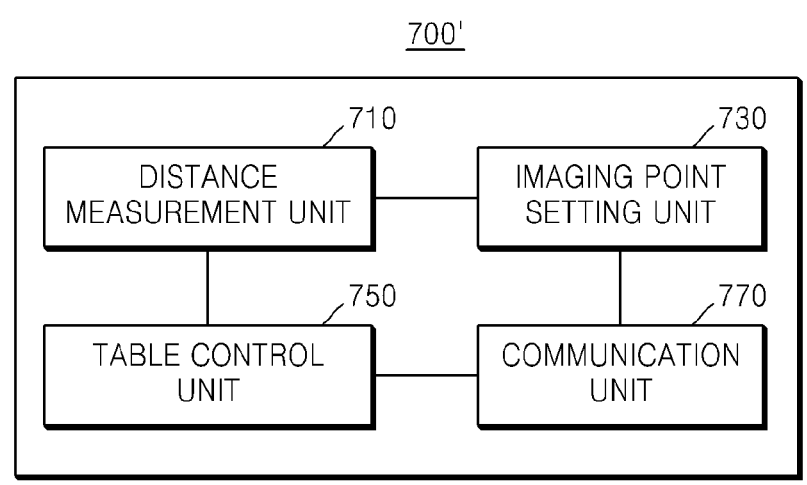
FIG. 7B is a block diagram illustrating elements of an apparatus for capturing a medical image, according to another embodiment of the present disclosure.

FIG. 7B is a block diagram illustrating elements of an apparatus, 700', for capturing a medical image, according to another embodiment of the present disclosure. Apparatus 700' further includes a communication unit 770 in addition to the elements of the apparatus 700 of FIG. 7A.

The communication unit 770 may receive an imaging point setting request from the wireless device 300, and when the imaging point setting unit 730 completes the setting of the imaging point, may transmit a message informing that the setting of the imaging point has been completed to the wireless device 300.

Also, the communication unit 770 may receive a table movement request from the wireless device 300 and may transmit the table movement request to the table control unit 750 so that the table control unit 750 adjusts a location of the table 110.

Figure 8:
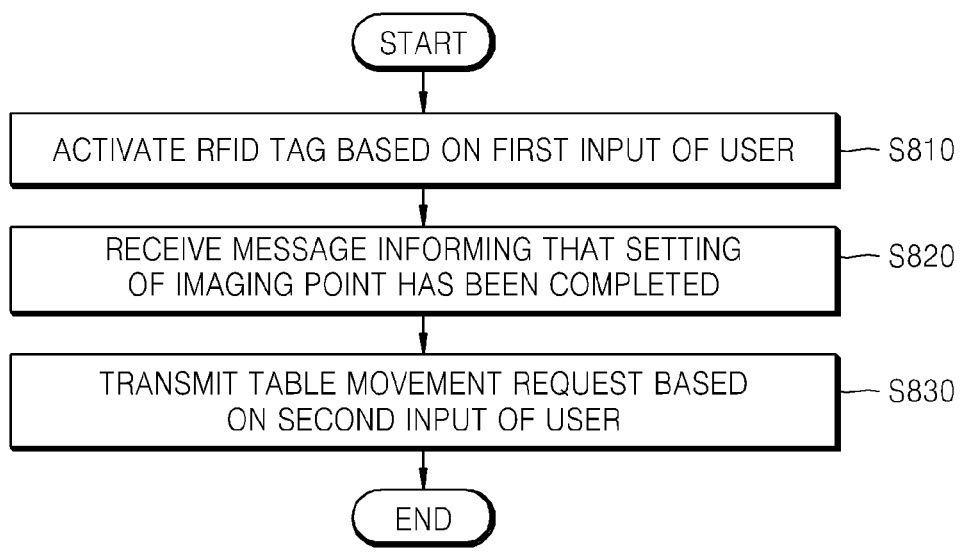
FIG. 8 is a flowchart illustrating a method of adjusting a location of the table, according to another embodiment of the present disclosure.

FIG. 8 is a flowchart illustrating an example method of adjusting a location of the table 110. The method may be performed by wireless device 300. In operation S810, an RFID tag attached to the wireless indicator 300 is activated based on a first input of the operator. The RFID tag may be a tag activated or inactivated by visible light or other form of energy. For instance, in response to detecting the first input of the operator, the wireless device 300 may activate the RFID tag by emitting visible light to the RFID tag. Since the RFID tag may be identified by an RFID reader, the wireless device 300 may transmit an imaging point setting request to the apparatus 100 when activating the RFID tag.

In operation S820, the wireless device 300 may receive from the apparatus 100 a message informing that the setting of the imaging point has been completed based on a location of the wireless device 300 identified by the RFID reader of the apparatus 100. As described above, when the operator positions the wireless device 300 at an arbitrary point, the apparatus 100 may set the imaging point by calculating a first axial distance between the wireless device 300 and a reference point. Next, the apparatus 100 may transmit to the wireless device 300 a message informing that the setting of the imaging point has been completed.

In operation S830, the wireless device 300 transmits a table movement request to the apparatus 100 based on a second input of the operator. However, if the above-noted message regarding the setting of the image point is not received from the apparatus 100 within a predetermined period of time after the RFID tag is activated, the wireless device 300 may output a message to the operator requesting a re-adjustment of the device 300's location. Since wireless communication apparatuses including an RFID reader and an RFID tag have a preset communication radius, when the wireless device 300 is located beyond the range of the preset communication radius, the transmitted signal may not be received by the reader. In this case, a message requesting that the device's location be re-adjusted is preferably output.

In an implementation, when the first axial distance between the reference point and the wireless device 300 exceeds a preset distance, the apparatus 100 may not set the imaging point. For example, when the wireless device 300 is located at a point outside the table 100 along the first axis, although the table 110 is entirely moved into the gantry 105 aperture, the imaging point may significantly differ from the reference point. In this case, the apparatus 100 does not set the imaging point and does not transmit a message informing that the setting of the imaging point has been completed to the wireless device 300. Accordingly, in this scenario the wireless device 300 may output a message requesting that the wireless device's location be re-adjusted.

Figure 9:
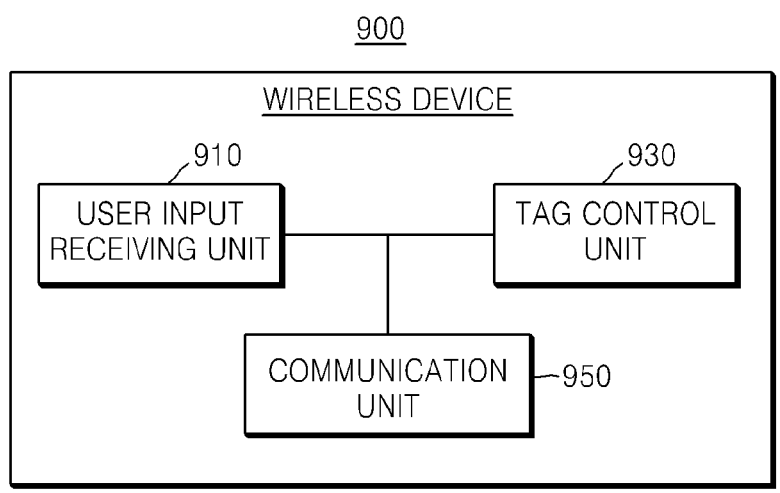
FIG. 9 is a block diagram illustrating elements of a wireless device according to an embodiment of the present disclosure.

FIG. 9 is a block diagram illustrating elements of a wireless device 900, which is an embodiment of wireless device 300 described above. Wireless device 900 includes a user input receiving unit 910, a tag control unit 930, and a communication unit 950.

The user input receiving unit 910 receives a user's input via a detection apparatus such as a voice recognition unit, a fingerprint recognition unit, a gesture recognition unit, or an eye recognition unit.

The tag control unit 930 activates or turns on an RFID tag attached to the wireless device 900 based on a first detected input of the operator.

The communication unit 950 receives from the apparatus 100 a message informing that setting of an imaging point has been completed based on a location of the wireless device 900 identified by an RFID reader of the apparatus 100, and transmits a table movement request to the apparatus 100 based on a second detected input of the operator.

Although not shown in FIG. 9, the wireless device 900 may further include an output unit (e.g. a display or speaker) that outputs a message requesting that a location of the wireless device 900 be re-adjusted when the message informing that the setting of the imaging point has been completed is not received from the apparatus 100 within a predetermined period of time after the RFID tag is activated.

Also, the wireless device 900 may further include a light pointer (not shown) that emits a narrow beam of light. The operator may check which point of the object is indicated by the wireless device 900 by viewing the light emitted by the light pointer. The operator may more accurately set the imaging point by using the light pointer.

Figure 10:
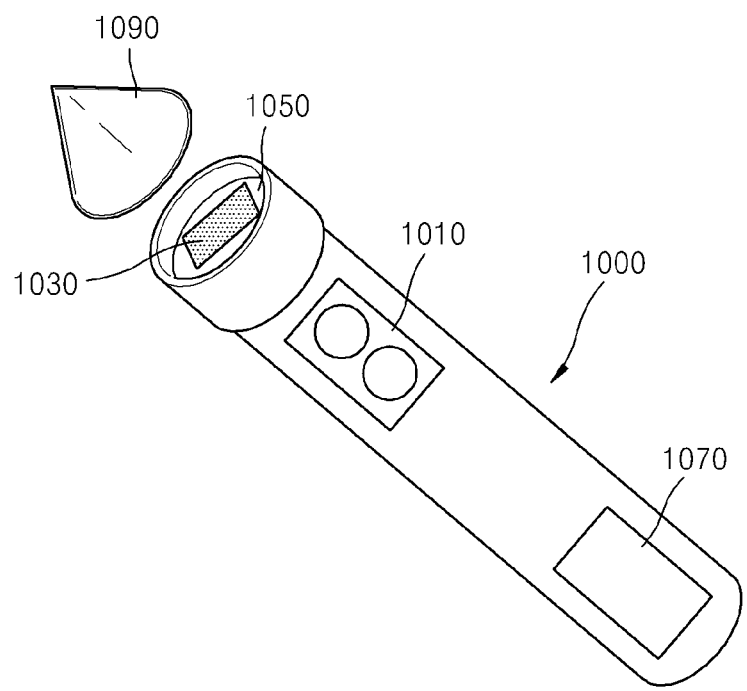
FIG. 10 is a view illustrating a wireless device according to an embodiment of the present disclosure.

FIG. 10 is a perspective view illustrating a wireless device 1000, which is an embodiment of the wireless device 300 described above. Wireless device 1000 may include a user input unit 1010, an RFID tag 1030, an output unit 1070, a light emitting unit 1050, and an RFID tag cap 1090 that protects the RFID tag 1030 from physical impact.

The user input unit 1010 has a button structure, allowing an operator to input a predetermined control command by pressing a button. The operator may press an imaging point setting button of the user input unit 1010 so that light is emitted to the RFID tag 1030 by the light emitting unit 1050. In this manner, the RFID tag 1030 may be activated. In addition, the emitted light is focused by the RFID tag cap 1090 so as to emit a narrow beam of light from the tag cap 1090. In this manner, the wireless device 1000 also functions as a light pointer. The operator may point the light beam to a desired imaging point on the object 10, which may be detected by the medical imaging apparatus to further aid in the table adjustment.

When the wireless device 1000 receives a message informing that setting of an imaging point has been completed from the apparatus 100, the wireless device 1000 may output the message through the output unit 1070. When the wireless device 1000 does not receive the message within a predetermined period of time after the RFID tag 1030 is activated, the wireless device 1000 may output a message through the output unit 1070 alerting the operator with a request to re-adjust a location of the wireless device 1000.

When the message informing that the setting of the imaging point has been completed is output through the output unit 1070, the operator may press a table movement button of the user input unit 1010, causing a table movement request to be transmitted to the apparatus 100.

Figure 11:
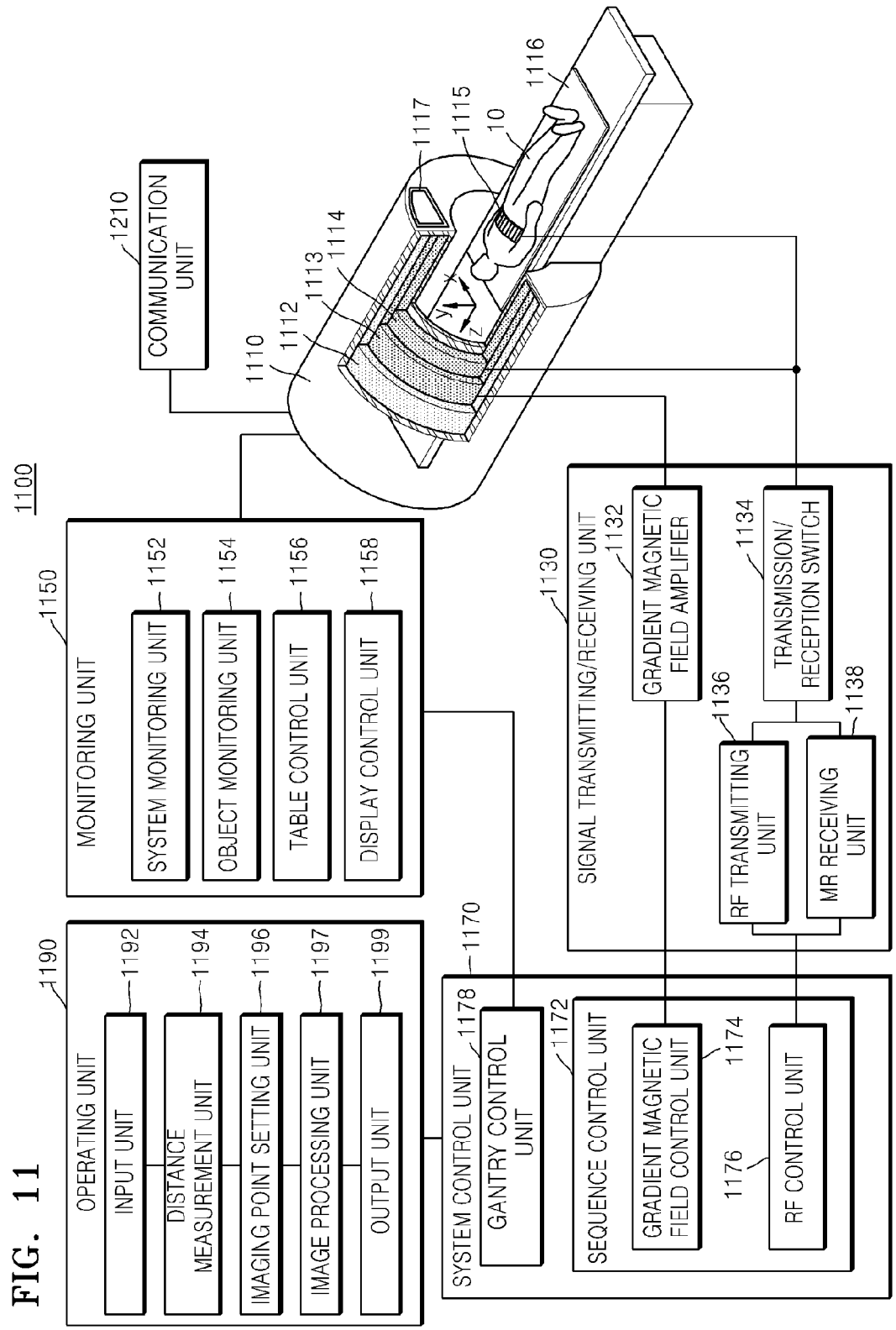
FIG. 11 is a block diagram illustrating elements of an apparatus for capturing a medical image, according to another embodiment of the present disclosure.

FIG. 11 is a block diagram illustrating elements of an apparatus 1100 for capturing a medical image (medical imaging apparatus), according to an embodiment of the present disclosure. FIG. 11 illustrates an MRI apparatus as the apparatus 1100. It is noted, however, that other types of medical imaging apparatus are available for use with the table positioning technology disclosed herein.

As shown in FIG. 11, the apparatus 1100 may include a gantry 1110 having a central within which an object 10 is moved for imaging, a signal transmitting/receiving unit 1130, a monitoring unit 1150, a system control unit 1170, an operating unit 1190, and a communication unit 1210.

The gantry 1110 blocks electromagnetic waves generated by a main magnet 1112, a gradient coil 1113, a fixed RF coil 1114, and a detachable RF coil 1115 from being radiated to the exterior. A static magnetic field and a gradient magnetic field are formed in a bore of the gantry 1110, and an RF signal is emitted to the object 10.

The main magnet 1112, the gradient coil 1113, and the fixed RF coil 1114 may be arranged in a predetermined direction of the gantry 1110. The predetermined direction may include a coaxial circumferential direction. The object 10 may lie on a table 1116 that may be inserted along a horizontal axis into the gantry 1110 aperture of a cylindrical shape.

The main magnet 1112 generates a static magnetic field for arranging, in a constant direction, magnetic dipole moments of atomic nuclei included in the object 10. As the static magnetic field generated by the main magnet 1112 is strong and uniform, a relatively precise and accurate MR image of the object 10 may be obtained.

The gradient coil 1113 includes X, Y, and Z coils that generate gradient magnetic fields in X, Y, and Z-axes that are perpendicular to one another. (It is noted here that the labels for the Y and Z directions used here differ from those used in the table adjustment operation described above.) The gradient coil 1113 may derive different resonance frequencies from different body parts of the object 10 and may provide location information of the different body parts of the object 10.

The fixed RF coil 1114 and the detachable RF coil 1115 may transmit an RF signal to a patient and may receive an MR signal emitted from the patient. In detail, the fixed RF coil 1114 and the detachable RF coil 1115 may transmit to a patient an RF signal having the same frequency as a frequency of a precession toward atomic nuclei that precess, and then may stop transmitting the RF signal and may receive an MR signal emitted from the patient.

For example, in order to change an atomic nucleus from a low energy state to a high energy state, the fixed RF coil 1114 and the detachable RF coil 1115 may generate an electromagnetic signal, for example, an RF signal, having RF characteristics corresponding to a type of the atomic nucleus and may apply the electromagnetic signal to the object 10. When the electromagnetic signal generated by the fixed RF coil 1114 and the detachable RF coil 1115 is applied to the atomic nucleus, the atomic nucleus may be changed from a low energy state to a high energy state. Next, when the electromagnetic signal generated by the fixed RF coil 1114 and the detachable RF coil 1115 is removed, the atomic nucleus to which the electromagnetic wave signal is applied may be changed from a high energy state to a low energy state so that electromagnetic waves having a Larmor frequency may be radiated. In other words, when the electromagnetic wave signal is no longer applied to the atomic nucleus, the atomic nucleus to which the electromagnetic wave signal is applied may be changed from a high energy state to a low energy state and thus electromagnetic waves having a Larmor frequency may be radiated. The fixed RF coil 1114 and the detachable RF coil 115 may receive an electromagnetic wave signal emitted from atomic nuclei in the object 10.

The fixed RF coil 1114 and the detachable RF coil 1115 may each be embodied as a single RF transmitting/receiving coil that functions to generate electromagnetic waves having RF characteristics corresponding to a type of atomic nuclei and to receive electromagnetic waves radiated from the atomic nuclei. Alternatively, the fixed RF coil 114 and the detachable RF coil 1115 may be respectively embodied as an RF transmitting coil that functions to generate electromagnetic waves having RF characteristics corresponding to a type of atomic nuclei and an RF receiving coil that functions to receive electromagnetic waves radiated from the atomic nuclei.

The detachable RF coil 1115 may be an RF coil for a body part of the object 10 such as a head RF coil, a breast RF coil, a leg RF coil, a neck RF coil, a shoulder RF coil, a wrist RF coil, or an ankle RF coil.

The detachable RF coil 1115 may communicate with an external apparatus in a wired and/or wireless manner, and may perform dual tune communication according to a communication frequency band.

Also, the detachable RF coil 1115 may include a birdcage coil, a surface coil, and a transverse electromagnetic (TEM) coil according to a structure of a coil. The detachable RF coil 1115 may include a transmission-only coil, a reception-only coil, and/or a combined transmission/reception coil according to a use. The detachable RF coil 1115 may include an RF coil of any of various channels such as 16 channels, 32 channels, 72 channels, and 144 channels according to the number of channels.

The gantry 1110 may further include a display unit 1117 that is located outside the gantry 1110, and a display unit (not shown) that is located inside the gantry 1110.

The signal transmitting/receiving unit 1130 may control a gradient magnetic field that is formed in a bore of the gantry 1110 according to a predetermined MR sequence, and may control an RF signal and an MR signal to be transmitted/received.

The signal transmitting/receiving unit 1130 may include a gradient magnetic field amplifier 1132, a transmission/reception switch 1134, an RF transmitting unit 1136, and an MR receiving unit 1138.

The gradient magnetic field amplifier 1132 may drive the gradient coil 1113 included in the gantry 1110, and may supply to the gradient coil 1113 a pulse signal for generating a gradient magnetic field under the control of a gradient magnetic field control unit 1174. Gradient magnetic fields in X, Y, and Z-axes may be combined by controlling a pulse signal supplied from the gradient magnetic field amplifier 1132 to the gradient coil 1113.

The RF transmitting unit 1136 and the MR receiving unit 1138 may drive the fixed RF coil 1114 and the detachable RF coil 1115. The RF transmitting unit 1136 may supply an RF pulse having a Larmor frequency to the fixed RF coil 1114 and the detachable RF coil 1115, and the MR receiving unit 1138 may receive an MR signal received by the fixed RF coil 1114 and the detachable RF coil 1115.

The transmission/reception switch 1134 may adjust directions in which an RF signal and an MR signal are transmitted/received. For example, the transmission/reception switch 1134 may enable an RF signal to be emitted to the object 10 by the fixed RF coil 1114 and the detachable RF coil 1115 during a transmission mode, and may enable an MR signal to be received from the object 10 by the fixed RF coil 1114 and the detachable RF coil 1115 during a reception mode. The transmission/reception switch 1134 may be controlled by a control signal from an RF control unit 1176.

The monitoring unit 1150 may monitor or control the gantry 1110 or devices mounted on the gantry 1110. The monitoring unit 1150 may include a system monitoring unit 1152, an object monitoring unit 1154, a table control unit 1156, and a display control unit 1158.

The system monitoring unit 1152 may monitor and control a state of a static magnetic field, a state of a gradient magnetic field, a state of an RF signal, a state of an RF coil, a state of the table 1116, a state of a device that measures body information of the object 10, a state of a power supply, a state of a heat exchanger, and a state of a compressor.

The object monitoring unit 1154 monitors a state of the object 10. In detail, the object monitoring unit 1154 may include a camera for observing a movement or a location of the object 10, a respiration measurement device for measuring a respiration of the object 10, an electrocardiogram (ECG) measurement device for measuring an ECG of the object 10, or a temperature measurement device for measuring a temperature of the object 10, and the respiration measurement device, the ECG measurement device, or the temperature measurement device may be attached to or detached from the gantry 1110.

The table control unit 1156 controls a movement of the table 1116 on which the object 10 lies. The table control unit 1156 may control a movement of the table 1116 according to a sequence control of a sequence control unit 1172. For example, when a moving image of the object 10 is to be captured, the table control unit 1156 may move the table 1116 continuously or intermittently according to a sequence control of the sequence control unit 1172. Accordingly, the object 10 may be imaged with a field of view (FOV) greater than a FOV of the gantry 1110.

Also, the table control unit 1156 may move the table 1116 into, or with respect to, the gantry 1110 aperture based on a first axial distance and a second axial distance calculated by a imaging point setting unit 1196, and may adjust a height of the table 1116.

The display control unit 1158 controls display units that are located outside and inside the gantry 1110 (e.g., on the exterior surface of gantry 1110 and at the surface of the gantry 1110 aperture, respectively). In detail, the display control unit 1158 may control the display units that are located outside and inside the gantry 1110 to be turned on/off, or may control a scene to be displayed on the display units. When a speaker is located inside or outside the gantry 1110, the display control unit 1158 may control the speaker to be turned on/off or a sound to be output through the speaker.

The system control unit 1170 may include the sequence control unit 1172 that controls a sequence of signals formed in the gantry 1110, and a gantry control unit 1178 that controls the gantry 1110 and devices mounted on the gantry 1110.

The sequence control unit 1172 may include the gradient magnetic field control unit 1174 that controls the gradient magnetic field amplifier 1132, and the RF control unit 1176 that controls the RF transmitting unit 1136, the MR receiving unit 1138, and the transmission/reception switch 1134.

The sequence control unit 1172 may control the gradient magnetic field amplifier 1132, the RF transmitting unit 1136, the MR receiving unit 1138, and the transmission/reception switch 1134 according to a pulse sequence received from an operating unit 1190. Here, the pulse sequence includes all information needed to control the gradient magnetic field amplifier 1132, the RF transmitting unit 1136, the MR receiving unit 1138, and the transmission/reception switch 1134, for example, information about an intensity, an application time, and an application timing of a pulse signal applied to the gradient coil 1113.

The operating unit 1190 may give pulse sequence information to the system control unit 1170, and may control an overall operation of the apparatus 1100.

The operating unit 1190 may include an input unit 1192, a distance measurement unit 1194, the imaging point setting unit 1196, an image processing unit 1197, and an output unit 1199.

The operator may input object information, parameter information, information about scan conditions, a pulse sequence, image synthesis, or a differential operation. The input unit 1192 may include a keyboard, a mouse, a trackball, a voice recognition unit, a gesture recognition unit, a touch screen, etc., and may include any of various input apparatuses which are known to one of ordinary skill in the art.

The distance measurement unit 1194 measures distances between a plurality of detection units that are arranged along a first axis and a wireless device that is positioned at an arbitrary point by the operator. The distance measurement unit 1194 may measure the distances between each of the plurality of detection units and the wireless device by using a time taken from when a distance measurement signal is emitted from each of the plurality of detection units to a time that the distance measurement signal reflected by the wireless device is received by each of the plurality of detection units. The distance measurement unit 1194 may measure distances between a plurality of second detection units that are arranged along a second axis, for example, an axis perpendicular to the first axis, and the wireless device.

The imaging point setting unit 1196 calculates a distance on the first axis (herein referred to as a first axial distance) between a reference point and the wireless device using the distances between the plurality of detection units and the wireless device and locations of the plurality of detection units relative to the reference point. The reference point may be preset, e.g., by the operator. The imaging point setting unit 1196 may set a point on the object 10 which is spaced by the first axial distance from the reference point as an imaging point.

Also, the imaging point setting unit 1196 may calculate a distance on a second axis (herein referred to as a second axial distance) between the reference point and the wireless device by using the distances between the plurality of second detection units and the wireless device and locations of the plurality of second detection units relative to the reference point.

The image processing unit 1197 may process an MR signal received from the MR receiving unit 1138, and may generate MR image data for the object 10. The image processing unit 1197 performs various signal processing functions such as amplification, frequency conversion, phase detection, low frequency amplification, and filtering on the MR signal received by the MR receiving unit 1138.

The image processing unit 1197 may store digital data in, for example, a k-space (for example, called a Fourier space or a frequency space) of a memory, and may reconstruct the digital data into image data through 2D or 3D Fourier transform. Image processing unit 1197 may perform synthesis or differential operation on the image data, if necessary. Examples of the synthesis may include pixel addition and maximum intensity projection (MIP). Also, the image processing unit 1197 may store in the memory (not shown) or an external server not only the reconstructed image data but also the image data on which the synthesis or the differential operation has been performed.

The various signal processing functions performed on the MR signal by the image processing unit 1197 may be performed in parallel. For example, a plurality of MR signals received by a multi-channel RF coil may be reconstructed into image data by applying in parallel signal processing functions on the plurality of MR signals.

The output unit 1199 may output the image data generated or reconstructed by the image processing unit 1197 to the operator. Output unit 1199 may further output information needed for the operator to manipulate the apparatus 1100 such as user interface (UI) information, user information, or object information. The output unit 1199 may include a speaker, a printer, a cathode-ray tube (CRT) display unit, an liquid crystal display (LCD) display unit, a plasma display panel (PDP) display unit, an organic light-emitting display (OLED) unit, a field emission display (FED) unit, a light-emitting diode (LED) display unit, a vacuum fluorescent display (VFD) unit, a digital light processing (DLP) display unit, a primary flight display (PFD) unit, a 3D display unit, and a transparent display unit, and may include any of various output apparatuses which are known to one of ordinary skill in the art.

Although the signal transmitting/receiving unit 1130, the monitoring unit 1150, the system control unit 1170, and the operating unit 1190 are separated from one another in FIG. 11, it will be understood by one of ordinary skill in the art that any of these units may be integrated with another component(s). For example, although the image processing unit 1197 converts an MR signal received by the MR receiving unit 1138 into a digital signal, the conversion to the digital signal may be directly performed by the MR receiving unit 1138, the fixed RF coil 1114, or the detachable RF coil 1115 with suitably integrated hardware.

The gantry 1110, the fixed RF coil 1114, the detachable RF coil 1115, the signal transmitting/receiving unit 1130, the monitoring unit 1150, the system control unit 1170, and the operating unit 1190 may be connected to one another in a wired or wireless manner. When the gantry 1110, the fixed RF coil 1114, the detachable RF coil 1115, the signal transmitting/receiving unit 1130, the monitoring unit 1150, the system control unit 1170, and the operating unit 1190 are connected in a wireless manner, an apparatus (not shown) for synchronizing clock signals therebetween may be further included. Communication between the gantry 1110, the fixed RF coil 1114, the detachable RF coil 1115, the signal transmitting/receiving unit 1130, the monitoring unit 1150, the system control unit 1170, and the operating unit 1190 may be high speed digital interface communication such as low voltage differential signaling (LVDS), asynchronous serial communication such as universal asynchronous receiver transmitter (UART), low latency network protocol such as controller area network (CAN), or optical communication, and any of various communication methods which are known to one of ordinary skill in the art may be used.

Figure 12:
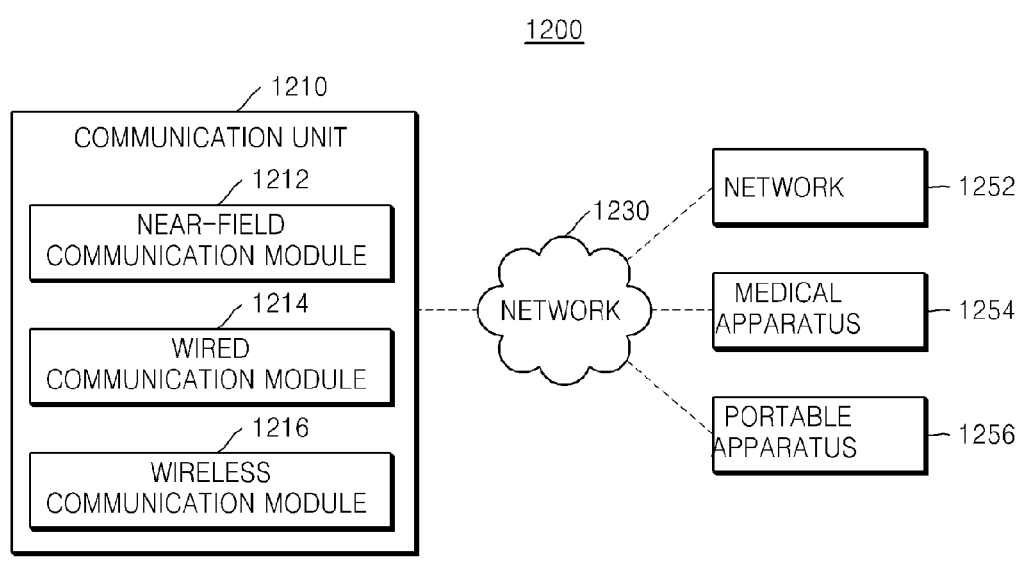
FIG. 12 is a block diagram illustrating a communication unit included in the apparatus of FIG. 11.

FIG. 12 is a block diagram illustrating an example communication unit 1210 included in the apparatus 1100 of FIG. 11. Communication unit 1210 may be electrically and/or communicatively connected to at least one of the gantry 1110, the signal transmitting/receiving unit 1130, the monitoring unit 1150, the system control unit 1170, and the operating unit 1190 of FIG. 11.

The communication unit 1210 may transmit and receive data to and from a hospital server or another medical apparatus in a hospital connected through a picture archiving and communication system (PACS), and may communicate data according to a digital imaging and communications in medicine (DICOM) standard.

As shown in FIG. 12, the communication unit 1210 may be connected to a network 1230 of a communication system 1200 in a wired or wireless manner, and may communicate with an external server 1252, an external medical apparatus 1254, or an external portable apparatus 1256.

In detail, the communication unit 1210 may transmit/receive data related to diagnosis of the object 10 through the network 1230, and may transmit/receive a medical image obtained by the external medical apparatus 1254 such as a CT apparatus, an MRI apparatus, or an X-ray apparatus. Furthermore, the communication unit 1210 may receive a diagnosis history or a treatment schedule of a patient from the server 1252 and may use the received diagnosis history or treatment schedule to diagnose the object 10. Also, the communication unit 1210 may perform data communication not only with the server 1252 or the external medical apparatus 1254 in the hospital but also with the portable apparatus 1256 such as a mobile phone, a personal digital assistant (PDA), or a notebook computer of a doctor or a client.

Also, the communication unit 1210 may transmit to an operator-accessible computing device through the network 1230 information about whether the apparatus 1100 is abnormal, or medical image quality information, and may receive feedback from the operator.

The communication unit 1210 may include one or more elements that may communicate with an external apparatus, for example, a near-field communication module 1212, a wired communication module 1214, and a wireless communication module 1216.

The near-field communication module 1212 refers to a module that performs near-field communication with a device within a predetermined distance. Examples of a near-field communication technology according to an embodiment of the present disclosure may include, but are not limited to, a wireless local area network (LAN), Wi-Fi, Bluetooth, Zigbee, Wi-Fi Direct (WFD), ultra wideband (UWB), infrared data association (IrDA), Bluetooth low energy (BLE), and near-field communication (NFC).

The wired communication module 1214 refers to a module for performing communication using an electrical signal or an optical signal. Examples of a wired communication technology may include wireless communication technologies using a pair cable, a coaxial cable, an optical fiber cable, and other wireless communication technologies that are apparent to one of ordinary skill in the art.

The wireless communication module 1216 transmits/receives a wireless signal to/from at least one of a base station, an external apparatus, and a server in a mobile communication network. The wireless signal may include a voice call signal, a video call signal, and various types of data according to text/multimedia message transmission/reception.

The afore-described embodiments of the present disclosure may be implemented with the use of an executable program, and may be executed by a general-purpose digital computer that runs the program by using a computer-readable recording medium.

Examples of the computer-readable medium are a magnetic recording medium (a read-only memory (ROM), a floppy disc, a hard disc, etc.), and an optical recording medium (a compact disk (CD)-ROM, a digital versatile disk (DVD), etc.).

Moreover, the above-described embodiments can be implemented in hardware, firmware or via the execution of software or computer code that can be stored in a recording medium such as a CD ROM, a Digital Versatile Disc (DVD), a magnetic tape, a RAM, a floppy disk, a hard disk, or a magneto-optical disk or computer code downloaded over a network originally stored on a remote recording medium or a non-transitory machine readable medium and to be stored on a local recording medium, so that the methods described herein can be rendered via such software that is stored on the recording medium using a general purpose computer, or a special processor or in programmable or dedicated hardware, such as an ASIC or FPGA. As would be understood in the art, the computer, the processor, microprocessor controller or the programmable hardware include memory components, e.g., RAM, ROM, Flash, etc. that may store or receive software or computer code that when accessed and executed by the computer, processor or hardware implement the processing methods described herein. In addition, it would be recognized that when a general purpose computer accesses code for implementing the processing shown herein, the execution of the code transforms the general purpose computer into a special purpose computer for executing the processing shown herein. The functions and process steps herein may be performed automatically or wholly or partially in response to user command. An activity (including a step) performed automatically is performed in response to executable instruction or device operation without user direct initiation of the activity. No claim element herein is to be construed under the provisions of 35 U.S.C. 112, sixth paragraph, unless the element is expressly recited using the phrase "means for."

While exemplary embodiments have been described above, it will be understood by one of ordinary skill in the art that various changes in form and details may be made therein without departing from the spirit and scope of the present invention as defined by the following claims. Hence, it will be understood that the embodiments described above are not limiting of the scope of the invention.

What is claimed is:

1. A method performed by an apparatus for capturing a medical image of an object to adjust a location of a table that supports the object, the method comprising:
measuring respective distances between a plurality of detection units arranged along an axis in a longitudinal direction of the table and an operator-adjustable wireless device;
calculating an axial distance on the axis between a reference point and the wireless device using the measured distances and respective locations of the plurality of detection units relative to the reference point;
moving the table with respect to a gantry aperture of the apparatus based on the calculated axial distance,
wherein,
the wireless device comprises a radio frequency identification (RFID) tag,
the plurality of detection units comprises a plurality of RFID readers, and
the measuring comprises measuring a distance between each of the plurality of RFID readers and the RFID tag by tracking transmission and reception times of signals exchanged between the RFID tag and the RFID readers.

2. The method of claim 1, wherein the moving the table comprises moving the table into the gantry aperture based on the calculated axial distance.

3. The method of claim 1, further comprising setting a point on the object which is separated by the calculated axial distance from the reference point as an imaging point,
wherein the moving comprises moving the table such that the imaging point is located in the gantry.

4. The method of claim 1, further comprising receiving an imaging point setting request from the wireless device.

5. The method of claim 4, further comprising, after the calculating of the axial distance is completed, transmitting a message to the wireless device indicating that the setting of the imaging point has been completed.

6. The method of claim 1, wherein the moving of the table comprises receiving a table movement request from the wireless device.

7. The method of claim 1, wherein the apparatus comprises a magnetic resonance imaging (MRI) apparatus or a computed tomography (CT) apparatus.

8. The method of claim 1, wherein the axis is a first axis, the plurality of detection units are a plurality of first detection units, the calculated axial distance is a first axial distance, moving the table comprises moving the table into the gantry aperture, and the method further comprises:
measuring respective distances between the wireless device and a plurality of second detection units arranged along a second axis;
calculating a second axial distance on the second axis between the reference point and the wireless device using the distances between the plurality of second detection units and the wireless device and locations of the plurality of second detection units relative to the reference point; and
adjusting a height of the table based on the calculated second axial distance.

9. A non-transitory computer-readable recording medium having embodied thereon a program including instructions which, when executed by a processor of an apparatus for capturing a medical image of an object, causes the apparatus to perform a method for adjusting a location of a table that supports the object, wherein the method comprises:
measuring respective distances between a plurality of detection units arranged along an axis in a longitudinal direction of the table and an operator-adjustable wireless device;
calculating an axial distance on the axis between a reference point and the wireless device using the measured distances and respective locations of the plurality of detection units relative to the reference point;
moving the table with respect to a gantry aperture of the apparatus based on the calculated axial distance,
wherein,
the wireless device comprises a radio frequency identification (RFID) tag,
the plurality of detection units comprises a plurality of RFID readers, and
the measuring comprises measuring a distance between each of the plurality of RFID readers and the RFID tag by tracking transmission and reception times of signals exchanged between the RFID tag and the RFID readers.

10. An apparatus for capturing a medical image of an object which adjusts a location of a table that supports the object, the apparatus comprising:
a processor that measures respective distances between a plurality of detection units that are arranged along an axis in a longitudinal direction of the table and an operator-adjustable wireless device, calculates an axial distance on the axis between a reference point and the wireless device using the measured distances and respective locations of the plurality of detection units relative to the reference point, and controls movement of the table with respect to a gantry aperture of the apparatus based on the calculated axial distance;
wherein, the wireless device comprises a radio frequency identification (RFID) tag, the plurality of detection units comprises a plurality of RFID readers, and the processor is configured to measure a distance between each of the plurality of RFID readers and the RFID tag by tracking transmission and reception times of signals exchanged between the RFID tag and the RFID readers.

11. The apparatus of claim 10, further comprising a communication unit that receives an imaging point setting request and a table movement request from the wireless device.

12. The apparatus of claim 10, wherein after the calculating of the axial distance is completed, a communication unit transmits a message informing that setting of an imaging point has been completed to the wireless device.

13. The apparatus of claim 10, wherein the processor measures a distance between each of the plurality of RFID readers and the RFID tag using a time taken from when a first signal is emitted from each of the plurality of RFID readers to a time that a second signal emitted from the RFID tag is received by each of the plurality of RFID readers.

14. The apparatus of claim 10, wherein:

the axis is a first axis, the plurality of detection units are a plurality of first detection units, the calculated axial distance is a first axial distance, the processor controls the movement of the table into the gantry aperture based on the calculated first axial distance;

the apparatus further comprises a plurality of second detection units arranged along a vertical axis and the processor further measures respective distances between the wireless device and the plurality of second detection units, and calculates a second axial distance on the vertical axis between the reference point and the wireless device using the distances between the plurality of second detection units and the wireless device and locations of the plurality of second detection units relative to the reference point, and the processor is further configured to control movement of the table by controlling adjustment of a height of the table based on the calculated second axial distance.

* * * * *